United States Patent [19]
Deutsch et al.

[11] Patent Number: 5,968,039
[45] Date of Patent: Oct. 19, 1999

[54] LASER DEVICE FOR PERFORMING CANAL SURGERY IN NARROW CHANNELS

[75] Inventors: Allan S. Deutsch, New York; Brett I. Cohen, Nanuet, both of N.Y.

[73] Assignee: Essential Dental Systems, Inc., South Hackensack, N.J.

[21] Appl. No.: 07/771,173

[22] Filed: Oct. 3, 1991

[51] Int. Cl.⁶ ..................................................... A61N 5/06
[52] U.S. Cl. ..................... 606/17; 606/2; 606/10; 606/15
[58] Field of Search .................... 128/395, 397, 128/398; 606/2–8, 10–19; 433/80–82, 215, 224, 229

[56] References Cited

U.S. PATENT DOCUMENTS

| | | | |
|---|---|---|---|
| 1,794,557 | 3/1931 | Symonds | 128/398 |
| 3,413,067 | 11/1968 | Froio | 128/398 |
| 4,503,853 | 3/1985 | Ota | 128/303.1 |
| 4,608,980 | 9/1986 | Aihara | 128/303.1 |
| 4,672,961 | 6/1987 | Davies | 606/7 |
| 4,693,244 | 9/1987 | Daikuzono | 128/303.1 |
| 4,818,230 | 4/1989 | Myers et al. | 433/215 |
| 4,826,431 | 5/1989 | Fujimura et al. | 433/29 |
| 4,842,390 | 6/1989 | Sottini et al. | 606/7 |
| 4,849,859 | 7/1989 | Nagasawa | 362/32 |
| 4,852,567 | 8/1989 | Sinofsky | 128/303.1 |
| 4,940,411 | 7/1990 | Vassiliadis | 606/3 |
| 4,988,163 | 1/1991 | Cohen et al. | 350/96.29 |
| 5,020,995 | 6/1991 | Levy | 433/215 |
| 5,037,421 | 8/1991 | Boutacoff et al. | 606/15 |

FOREIGN PATENT DOCUMENTS

| | | |
|---|---|---|
| 8908432 | 9/1989 | WIPO . |
| 9001907 | 3/1990 | WIPO . |

*Primary Examiner*—David M. Shay
*Attorney, Agent, or Firm*—Gottlieb, Rackman & Reisman, P.C.

[57] ABSTRACT

A laser apparatus for removing hard and soft tissue from a narrow channel has at its cutting end a configuration that causes the laser light to emerge in an annular region and not apically.

7 Claims, 2 Drawing Sheets

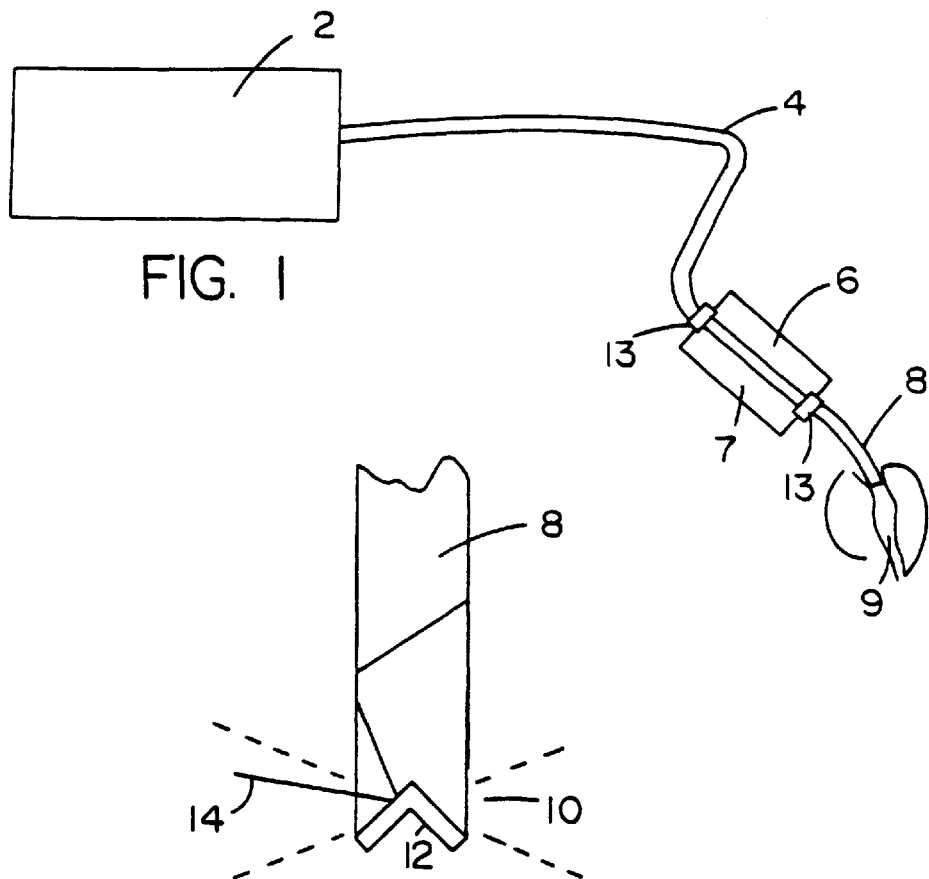
FIG. 1
FIG. 2
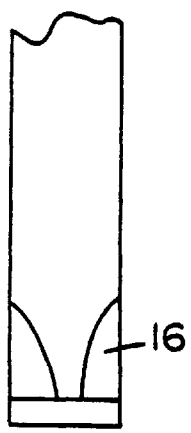
FIG. 4
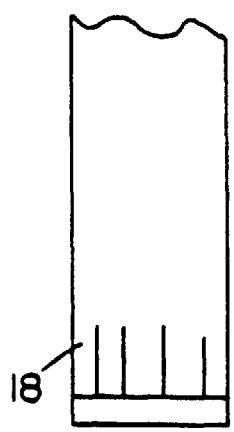
FIG. 5

LASER DEVICE FOR PERFORMING CANAL SURGERY IN NARROW CHANNELS

BACKGROUND OF THE INVENTION

This invention relates to surgical apparatus for performing root canal procedures in narrow channels employing laser energy to effect the removal of tissue from, for example, the root canal of a tooth or removal of tumors from narrow arteries (angeoplasty) or narrow ducts.

A common endodontic procedure is the removal of dental pulp and dentin walls from the root canal of a tooth with a diseased nerve preparatory to filling the root canal with a cement and prosthesis which supports a crown. The removal of the pulp and the dentinal walls has traditionally been accomplished by the use of drills to penetrate the crown of the tooth, followed by mechanical extraction of the pulp from the root canal and mechanical enlargement of the canal walls. The process is made complicated by the fact that the entire nerve must be removed from the root canal, but it is important that the endodontist not penetrate the end of the root canal into the underlying living tissue and open up channels for infection. If in the process of removing the pulp and enlarging the canal walls, the tooth structure is perforated, failure may ensue because of an inadequate seal resulting in bacterial growth in the end of the tooth. In addition, the traditional file may break when cleaning the canal preventing proper sealing and an inadequately sealed root canal will result. A great deal of endodontal technique consists in methods for terminating the removal of tissue at the precise point where the root canal exits the tooth.

The use of lasers of sufficient intensity to excise the tissue in surgical procedures is well known. What is required is laser light of sufficient intensity and precise focus to enable the removal of the tissue accompanied by sufficient exit channels for the waste products of the surgical removal. In many instances, the intense heat of the laser releases gases which require exit channels.

U.S. Pat. No. 5,020,995 disclosed a method and apparatus for performing endodontic treatments that involve removing tissue from the walls of a tooth canal by the use of laser radiation. The method and apparatus of that disclosure requires that a succession of pulses having appropriate energy levels, duration and repetition rate be employed. The patent discloses that the optical fiber that carries the laser radiation be given "a suitable length and diameter to be introduced into a canal". Col. 4, line 13. No further disclosure of configuration of the optical fiber is stated.

PCT Publication WO 90/01907 discloses a dental laser assembly for dental surgery employing a pulsed Nd:YAG beam delivered through an optical fiber. In general, the laser emerges from the fiber and is focused by a columnating lens and mirror arrangement to a point displaced from the end of a handpiece in an orientation similar to that of the tip of a dental drill. A second visible HeNe laser beam is emitted coaxial with the first so that the "cutting tip" is rendered visible. The publication also discloses that high energy levels between 100 Mj/pulse and 5 J/pulse are suitable for endodontic procedures such as root canals, apicoectomies and pulpectomies on a tooth. For this purpose a laser tip 212 (FIG. 10) is inserted into the opened pulp chamber and the laser used to eradicate the soft tissue in the pulp chamber. No further description of the configuration of the laser tip is given and the figure shows a pencil point configuration. There is no discussion of modifications of the end of the optic fiber or laser tip to particularly suit it for use in endodontic procedures.

PCT publication WO 89/08432 discloses a laser device for dental applications, particularly for removing enamel and dentin. It suggests the use of a conical or frustro-conical contacting tip to concentrate the laser energy at its apex.

There has been some concern on the part of surgeons who use lasers as scalpels that the laser beam not emerge freely from the end of the scalpel so as to require precise positioning of the scalpel at a distance from the incision. Devices have been suggested which employ fiber optic conduit means for the laser beam and terminate in configurations which cause the laser beam to emerge close to the end of the fiber optic. In this way, the surgeon can control the position of the cut in the same way that he would with a conventional scalpel, namely, by contacting the surface of the tissue to be excised with the tip of the scalpel, which is in this case, the tip of the fiber optic.

A BRIEF DESCRIPTION OF THE INVENTION

An improvement in the conventional surgical laser scalpel has been achieved adapting it to improved performance for root canal-type surgery. In this improvement, the tip of the fiber optic is adapted to cause the incising laser light to emerge close to the tip, but in an annular pattern generally close to a plane orthogonal to the axis of the optical fiber. This minimizes the quantity of laser radiation aligned along the axis of the fiber optic at the tip. In this way the laser device cuts laterally into the tissue within the root canal and not axially. This substantially prevents the scalpel from bursting downwards through the root canal at unintended rates. A 100 micron diameter (or more) file is inserted to provide a channel for insertion of the optical fiber which is then inserted to the full length of the channel. There is no danger of the optical fiber penetrating the tooth when the laser is energized since it does not cut apically. Cutting laterally is accomplished during removal of the fiber optic from the channel.

The invention contemplates a hand-held apparatus (except for the laser source) having both a removable fiber optic tip for the hand piece and a disposable tip. The device is also adapted to root canal therapy requiring removal of both hard and soft tissues by varying the intensity of the laser light.

The laser which is employed may be in HO-YAG or an ER-YAG laser. The essential difference between these lasers is the wavelength of the laser radiation which they provide.

The special fiber optic tip is capable of removing the pulp and cutting into the dentin walls of the root canal. The fiber optic tip is approximately 100 microns in outer diameter of which 5 to 10 microns can be sheathing and can be up to 600 microns in diameter. The configuration of the laser light can be achieved either through the use of silver mirrors or the configuration of the outer portion of the fiber optic is such that the light emerges in the shape of a donut, able to cut between 0.1 to 0.4 millimeters.

It is an object of the invention to provide an endodontic laser apparatus having a tip portion from which the laser light emerges in an annular region and not apically.

It is a further object of the invention to provide a disposable fiber optic tip and interchangeable handset for accomplishing this purpose.

BRIEF DESCRIPTION OF THE DRAWINGS

FIG. 1 shows the laser apparatus of the present invention.

FIG. 2 shows a first embodiment of the cutting head of the present invention.

FIG. 4 is a cross-section view of a cutting head of the present invention having a doped region.

FIG. 5 is a cross-section view of a cutting head of the present invention having an etched region.

DETAILED DESCRIPTION OF THE PREFERRED EMBODIMENT

Figure 3A:
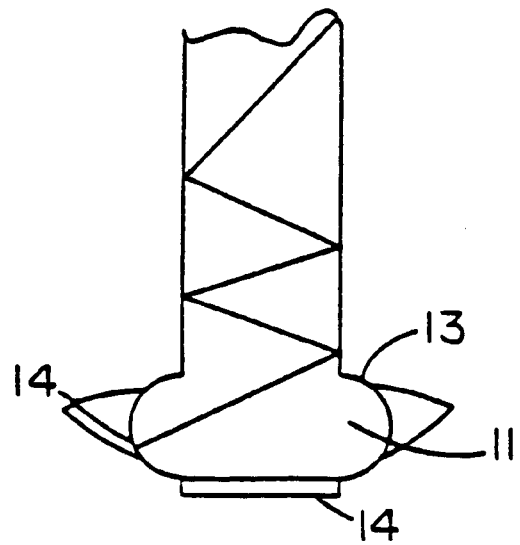
FIG. 3(a) and FIG. 3(b) show alternative cutting heads of the present invention in cross-section.

The invention comprises a laser emitting device 2, for example, one employing HO-YAG or ER-YAG as its lasing material and providing laser light with an intensity of approximately 5 watts into an optical fiber 4 having a diameter of approximately 100 microns up to 600 microns. The fiber optic 4 enters a handpiece 6 which may simply be a cylindrical hollow holder 7 of which captures the optical fiber that passes through it and terminates in the cutting head 8. The preferred embodiment has the optical fiber 4 terminating at a connector in the handpiece and a separate portion of optical fiber continuing through to the cutting head 8. Fittings 13 may be provided so that the handpiece 6 is removable from the optical fiber, together with the cutting head. Similarly, the cutting head 8 may be removable from the distal end of the handpiece and may be made disposable so that different ones could be used for different root canal lengths and different patients.

The cutting head 8 comprises the tip portion 10 which preferably has a conical indentation with a silvered surface 12. The conical indentation results in the laser rays which pass along the axis of the optical fiber reflecting and emerging transversely from the tip portion along the ray path 14 as shown in FIG. 2. Since the laser rays fill the fiber and are reflecting off the internal walls, the resulting emerging rays fill a slightly diverging annular region, which is depicted in cross section by the dotted lines in FIG. 2. If desired, the conical surface 12 of FIG. 2 may have curved walls to provide a focusing or defocusing effect. Because of the silvered end surface, virtually no laser radiation is leaving apically from the tip portion 10. They therefore cut laterally into the root canal 9 of FIG. 1.

Figure 3B:
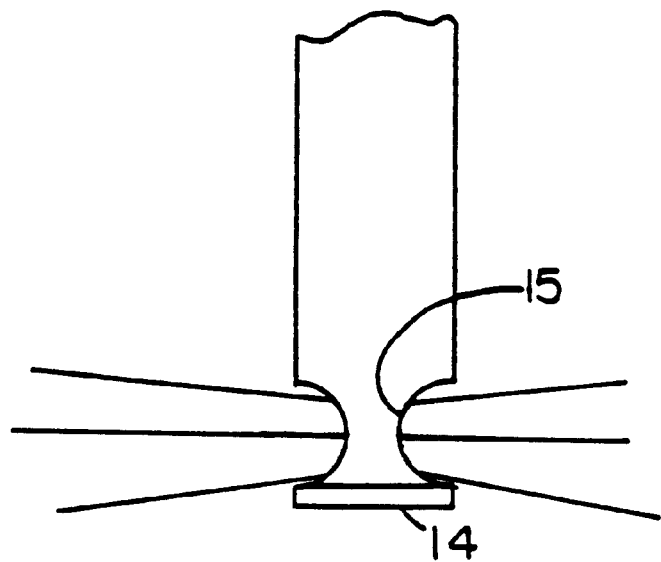

FIG. 3 shows an alternative embodiment in (a) in which the cutting head 8 terminates in a bulbous portion 13, which can be formed during the fabrication of the disposable tip portion. This may be formed either by molding or by heating and deforming the optical fiber. Because of the shape of the bulbous region 13 having a convex rounded external surface, a certain amount of focusing takes place as the light emerges from the optic fiber, and therefore the annular region is narrower for distances removed from the axis of the optical fiber. This has the advantageous effect of focusing the light into a converging disk-shaped region as shown in FIG. 3 where the intensity maximum occurs along a circular path, which is depicted in cross section by the circle 14. This keeps the light fairly close to the end of the tip portion, therefore concentrating its intensity. In an alternative embodiment as shown in FIG. 3(b), a concave region is formed wherein the light would be defocused as it emerges from the optic fiber. This would result in a diverging annular region much as is the case with the silvered end surface of the conical indentation. Either of these embodiments will provide acceptable results if the laser intensity is sufficient.

Other optical phenomena may be used to cause the light to emerge at the end of the tip portion of the optic fiber. In FIG. 4 is depicted a doped region 16 terminating in a silvered region that prevents apical emergence of the laser beam. The dopant is chosen to have a different index of refraction than the remainder of the optical fiber and cause refraction of the laser light directing it at angles of incidence to the cylindrical walls of the optical fiber less than Brewster's angle that will cause it to emerge from the fiber.

FIG. 5 shows a further embodiment in which diffraction phenomena are used to cause the laser light to leave the tip of the optic fiber. As shown in FIG. 5, the end of the optic fiber is provided with etch markings 18. The etch markings can be chosen in accord with the wavelength of the light so that diffraction effects occur and the primary maxima of the diffraction pattern will concentrate the light causing it to emerge from the optic fiber again in an annular region whose extent is determined by the height of the etched region along the axis of the apparatus.

In use, the endodontist would prepare the tooth by removing a portion of the crown and exposing the root canal. Using the handpiece, the cutting head would be placed into the canal and laser light passed into and axially outwards in an annular array from the tip of the laser device. The laser may be used in a wet field of NaOCl and this will increase the effectiveness of the sterility of the process. The intense laser beam cauterizes the tissue and provides a clean and sterile channel into the tooth. The length of cutting can be controlled by trimming the length of the cutting head or by providing interchangeable cutting heads of different length, much as is done with current techniques where various length pulp removal tools are provided for the endodontist. The depth or penetration of lateral cut is varied by the power intensity of the laser source.

The particular intensity and pulsation rates and other properties of the laser are not critically different from those known in the prior art for similar purposes. The configuration of the tip may be affected by the selection of the laser if the refractive properties of the fiber optic material are wavelength dependent. If there is significant dispersion of light in the optic fiber, it may be necessary to select particular wavelengths having these geometrical properties in mind to provide the appropriate refraction.

Although the invention has been disclosed in terms of several embodiments, it should be understood that the invention is not limited merely to those embodiments, but includes everything called for in the following claims.

We claim:

1. An endodontic laser apparatus for removing tissue from a root canal comprising laser light generating means for providing a coherent beam of intense light into an optical fiber, said fiber adapted to conduct the laser light by internal reflection to a distal end terminating in a tip portion adapted to divert the laser light from the optical fiber in an annular pattern not extending a substantial axial distance from the tip of the fiber, wherein tip portion is disposable and is removably held in a handpiece through which the fiber optic passes.

2. The endodontic laser apparatus of claim 1 wherein said handpiece comprises a portion of said optical fiber and is detachable together with a cutting head from the remainder of the fiber.

3. An endodontic laser apparatus for removing tissue from a root canal comprising laser light generating means for providing a coherent beam of intense light into an optical fiber, said fiber adapted to conduct the laser light by internal reflection to a distal end terminating in a tip portion adapted to divert the laser light from the optical fiber in an annular pattern not extending a substantial axial distance from the tip of the fiber, wherein said tip portion comprises a cylinder having a convex bulbous termination and an apical end wherein said light traveling along said optical fiber emerges focused in an annular pattern spaced from the apical end.

4. An endodontic laser apparatus for removing tissue from a root canal comprising laser light generating means for providing a coherent beam of intense light into an optical fiber, said fiber adapted to conduct the laser light by internal reflection to a distal end terminating in a tip portion adapted to divert the laser light from the optical fiber in an annular pattern not extending a substantial axial distance from the tip of the fiber, wherein said tip portion comprises a cylinder having a concave bulbous termination wherein said light travelling along said optical fiber emerges defocused in an annular pattern.

5. An endodontic laser apparatus for removing tissue from a root canal comprising laser light generating means for providing a coherent beam of intense light into an optical fiber, said fiber adapted to conduct the laser light by internal reflection to a distal end terminating in a tip portion adapted to divert the laser light from the optical fiber in an annular pattern not extending a substantial axial distance from the tip of the fiber, wherein said tip portion comprises a cylindrical shell doped region having an index of refraction that varies from the fiber away from said tip and that causes the laser light to emerge in an annular pattern.

6. An endodontic laser apparatus for removing tissue from a root canal comprising laser light generating means for providing a coherent beam of intense light into an optical fiber, said fiber adapted to conduct the laser light by internal reflection to a distal end terminating in a tip portion adapted to divert the laser light from the optical fiber in an annular pattern not extending a substantial axial distance from the tip of the fiber, wherein said tip portion comprises a cylindrical surface having etch lines adapted to cause laser light reaching the tip portion to undergo diffraction and emerge from the fiber optic in an annular region.

7. A method for removing tissue from a narrow channel extending along its length to its apical tip comprising inserting into the full length of the narrow channel an optical fiber adapted to conduct laser light by internal reflection to a distal end, said end terminating in a tip portion adapted to divert the laser light from the optical fiber in an annular pattern not extending a substantial axial distance from the tip of the fiber, energizing a laser adapted to output said laser light into said optical fiber, withdrawing the optical fiber from the channel while the laser is energized, wherein said laser causes lateral non-apical cutting of tissue in the channel along the length of the channel.

* * * * *